Figure 1:
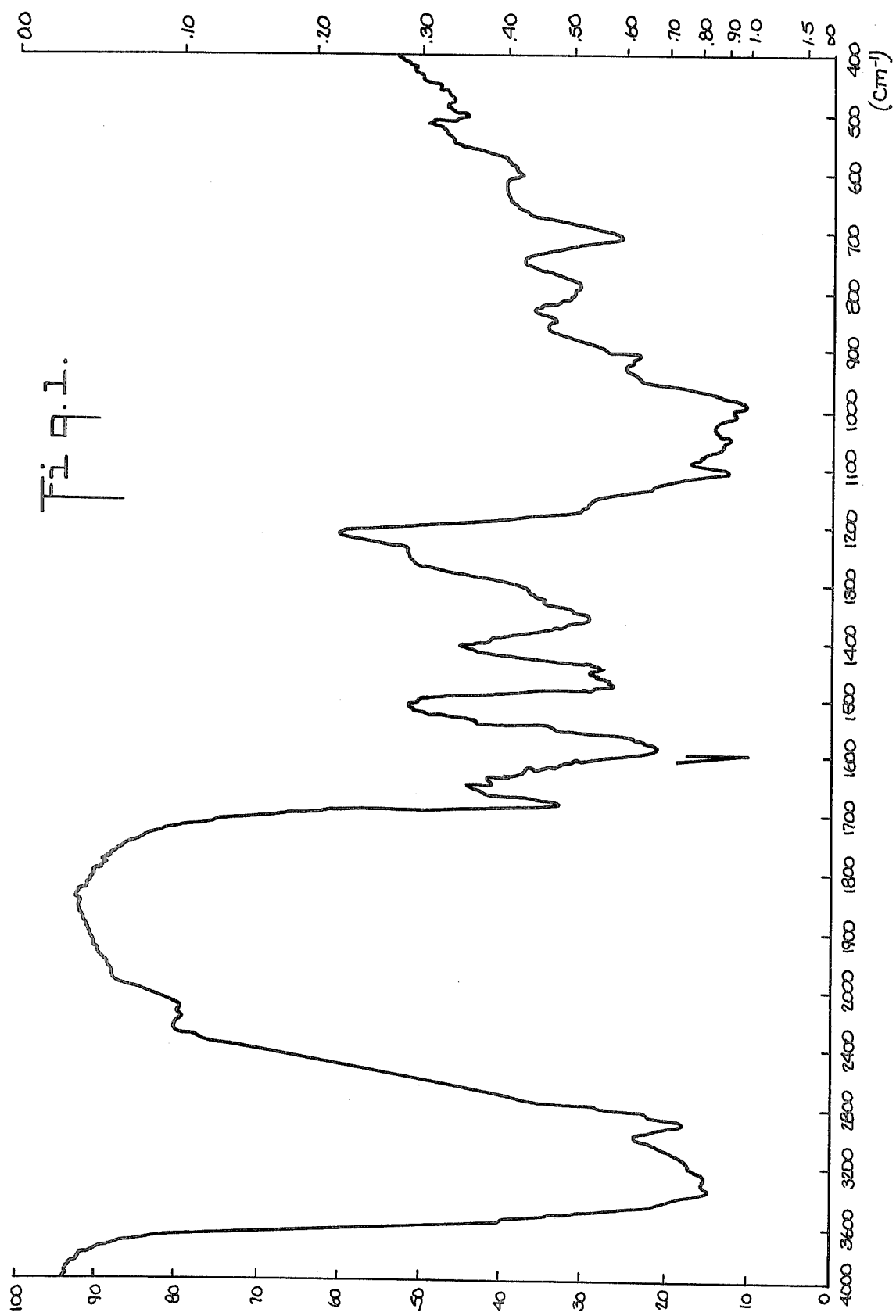

United States Patent [19]

Takahashi et al.

[11] 4,209,612
[45] Jun. 24, 1980

[54] FORTIMICIN FACTORS KF AND KG AND PROCESS FOR PRODUCTION THEREOF

[75] Inventors: Keiichi Takahashi, Machida; Takao Iida, Tokyo; Kunikatsu Shirahata, Machida; Masahiro Sugimoto; Shinzo Ishii, both of Shizuoka; Ryo Okachi; Takashi Nara, both of Tokyo, all of Japan

[73] Assignee: Abbott Laboratories, North Chicago, Ill.

[21] Appl. No.: 957,845

[22] Filed: Nov. 6, 1978

[30] Foreign Application Priority Data

Nov. 7, 1977 [JP] Japan ................................ 52-133305

[51] Int. Cl.² .............................................. C078 15/22
[52] U.S. Cl. ................................. 536/17 R; 424/181; 435/80; 536/18
[58] Field of Search .......................................... 536/17

[56] References Cited

U.S. PATENT DOCUMENTS

| 4,091,032 | 5/1978 | Tadanier et al. ........................ 536/17 |
| 4,124,756 | 11/1978 | Martin et al. ........................... 536/17 |

*Primary Examiner*—Johnnie R. Brown
*Attorney, Agent, or Firm*—Fitzpatrick, Cella, Harper & Scinto

[57] ABSTRACT

New antibiotic compounds, Fortimicin factors KF and KG are produced by fermentation of microorganisms belonging to the genus Micromonospora. The antibiotic compounds are accumulated in the culture liquor and are isolated therefrom.

2 Claims, 4 Drawing Figures

FORTIMICIN FACTORS KF AND KG AND PROCESS FOR PRODUCTION THEREOF

RELATED APPLICATIONS

The present invention is related generally to the inventions disclosed in U.S. Pat. No. 3,931,400 issued Jan. 6, 1976 for Fortimicin B and Process For Production Thereof; U.S. Pat. No. 3,976,768 issued Aug. 24, 1976 for Fortimicin A and Process For Production Thereof; U.S. Pat. No. 4,048,015 issued Sept. 13, 1977 for Fortimicin C and Process for Production Thereof; and U.S. patent application Ser. No. 845,970, filed Oct. 27, 1977 for Fortimicin Factors D and KE and Processes for Production Thereof.

BACKGROUND OF THE INVENTION

The present invention relates to new compositions of matter having antibacterial properties, namely Fortimicin KF and Fortimicin KG. The invention also pertains to the production of Fortimicin KF and/or Fortimicin KG by culturing a microorganism belonging to the genus Micromonospora, which is capable of producing one or both of the active substances in a nutrient medium, until antibacterial activity is detected in the culture liquor and then isolating at least one of the active substances therefrom.

Antibiotics which exhibit activity against a broad spectrum of bacteria are always in demand. To this end, it has been found that when certain strains of Micromonospora are cultured in a nutrient medium, several antibiotic substances are produced in the culture liquor. Specifically, Fortimicin factors A, B, C, D and KE have been isolated from the culture liquor of *Micromonospora olivoasterospora* MK-70 (ATCC 21819) (FERM-P No. 1560) and have the following structural formulae:

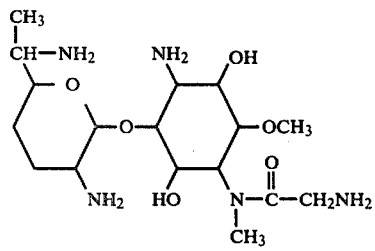

Fortimicin A

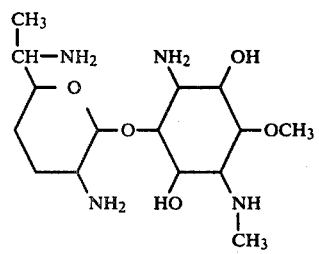

Fortimicin B

Fortimicin C

Fortimicin D

Fortimicin KE

The chemical, physical and biological properties of these antibiotics and the processes for the production thereof are explained in detail in the specifications of the aforementioned United States Patents and application.

It has now been found that *Micromonospora olivoasterospora* MK-70, when cultured, liberates two further active substances. A study of the chemical, physical and biological properties of these active substances indicates that the compositions of matter are new antibiotics which have now been named Fortimicin KF and Fortimicin KG.

SUMMARY OF THE INVENTION

In accordance with the present invention, novel antibiotics, Fortimicin factors KF and KG, are produced by fermentation of a microorganism belonging to the genus Micromonospora which is capable of producing one or both of said factors, in a nutrient medium until substantial antibacterial activity is detected in the culture liquor. At the completion of culturing, the active fractions containing Fortimicin KF or Fortimicin KG are isolated from the culture liquor by known means such as by ion exchange resin treatment.

Fortimicin factors KF and KG exhibit broad antibacterial activity, and are, therefore, useful inter alia to clean and sterilize laboratory glassware and surgical instruments, and may also be used in combination with soaps, detergents and wash solutions for sanitation purposes.

Included in the composition of matter aspect of the invention are the pharmaceutically acceptable nontoxic acid addition salts of Fortimicin KF and Fortimicin KG including the mineral acid addition salts such as hydrochloride, hydrobromide, hydroiodide, sulfate, sulfamate, carbonate, nitrate and phosphate and the organic acid addition salts such as maleate, acetate, citrate, oxalate, succinate, benzoate, tartrate, fumarate, malate, mandelate, ascorbate and the like.

DESCRIPTION OF THE INVENTION

The physicochemical properties of the free base of Fortimicin KF are as follows:
(1) A basic white powder
(2) The elementary analytical value found:
    C=47.72%, H=8.55%, N=15.77%
(3) Melting point: 69°-72° C.
(4) Ultraviolet absorption spectrum:
    Ultraviolet absorption spectrum of an aqueous solution of the substance does not show characteristic maximum absorption between 220 nm and 360 nm but only shows terminal absorption.
(5) Specific rotation: $[\alpha]_D^{24} = +127°$ (c=0.615, $H_2O$)
(6) Infrared absorption spectrum:
The infrared absorption spectrum measured in KBr is illustrated in FIG. 1. The free base of Fortimicin KF shows maximum absorption at the following wavenumbers ($cm^{-1}$): 3350, 2900, 1680, 1585, 1472, 1440, 1365, 1110.
(7) Color reactions:

| Ninhydrin reaction: | positive |
| --- | --- |
| Potassium permanganate reaction: | positive |
| Elson-Morgan's reaction: | negative |
| Biuret reaction: | negative |

Figure 2:
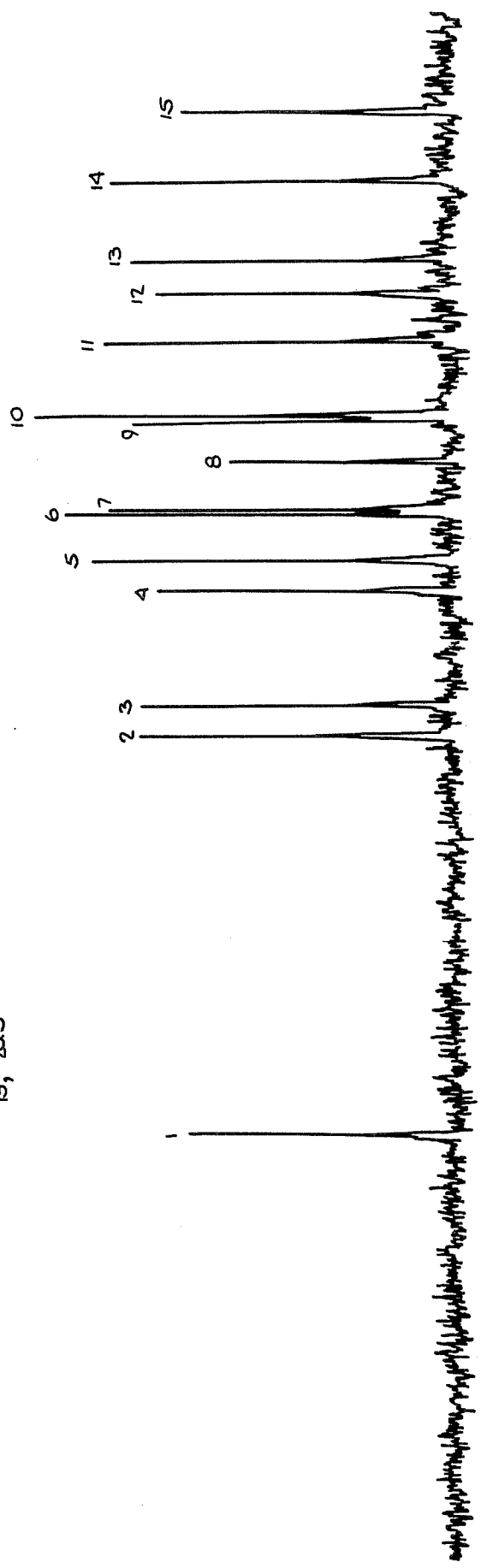

(8) The CMR spectrum of Fortimicin KF, measured in a deuterium oxide solution (pD=10.7) using a JEOL PFT-100A spectrometer is illustrated in FIG. 2.
(9) The mass spectrum of the substance reveals the following M ion and fragment ions. The formula in parentheses means the composition formula obtained by high resolution mass spectrometry.

| m/e | 332 ($C_{14}H_{28}N_4O_5$), | |
| --- | --- | --- |
| | 247 ($C_{10}H_{21}N_3O_4$), | 235 ($C_9H_{19}N_2O_5$), |
| | 217 ($C_9H_{17}N_2O_4$), | 189 ($C_8H_{17}N_2O_3$) |

From the result of the mass spectrometry, the molecular weight of the substance is calculated to be 332 and the molecular formula is calculated to be $C_{14}H_{28}N_4O_5$. The elementary analytical values of the substance (hydrated with 1 mole of $H_2O$) as calculated from the molecular formula are C=47.99%, H=8.63% and N=15.99%.
(10) Based on the foregoing physicochemical data, the structural formula of Fortimicin KF is considered to be as follows:

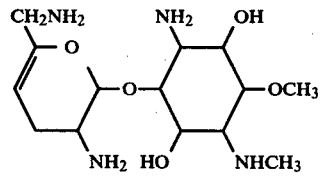

(11) The free base of Fortimicin KF is very soluble in water, soluble in methanol and slightly soluble in ethanol and acetone but is insoluble in organic solvents such as chloroform, benzene, ethyl acetate, butyl acetate, ether, butanol, petroleum ether, n-hexane, etc.

Figure 3:
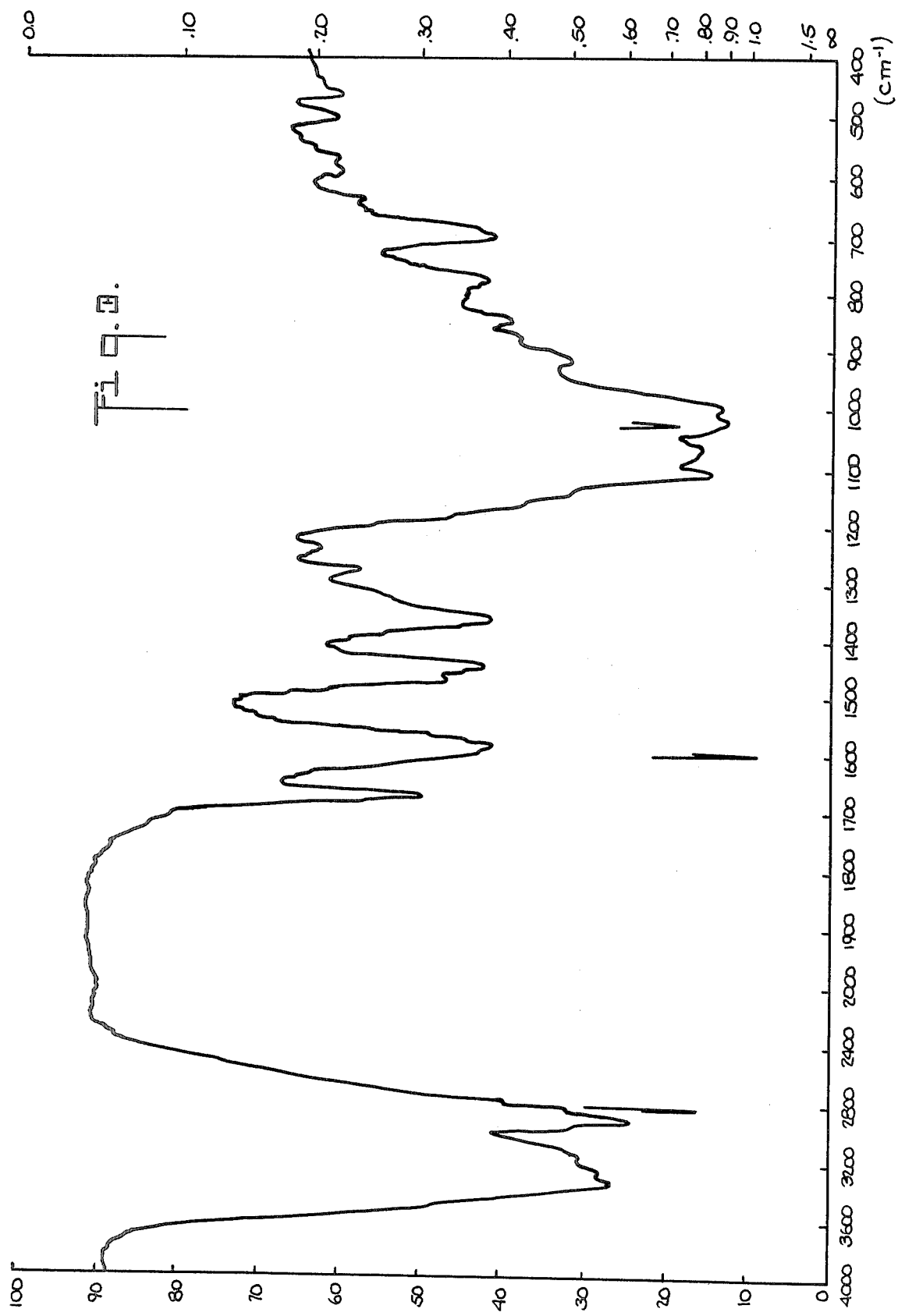

The physicochemical properties of the free base of Fortimicin KG are as follows:
(1) A basic white powder
(2) The elementary analytical value found:
    C=47.07%, H=9.19%, N=14.49%
(3) Melting point: 72°-74° C.
(4) Ultraviolet absorption spectrum:
    Ultraviolet absorption spectrum of an aqueous solution of the substance does not show characteristic maximum absorption between 220 nm and 360 nm but only shows terminal absorption.
(5) Specific rotation: $[\alpha]_D^{24} = +90°$ (c=0.33, $H_2O$)
(6) Infrared absorption spectrum:
    The infrared absorption spectrum measured in KBr is illustrated in FIG. 3. The free base of Fortimicin KG shows maximum absorption at the following wavenumbers ($cm^{-1}$): 3350, 1678, 1590, 1448, 1365, 1110.
(7) Color reactions:

| Ninhydrin reaction: | positive |
| --- | --- |
| Potassium permanganate reaction: | positive |
| Elson-Morgan's reaction: | negative |
| Biuret reaction: | negative |

Figure 4:
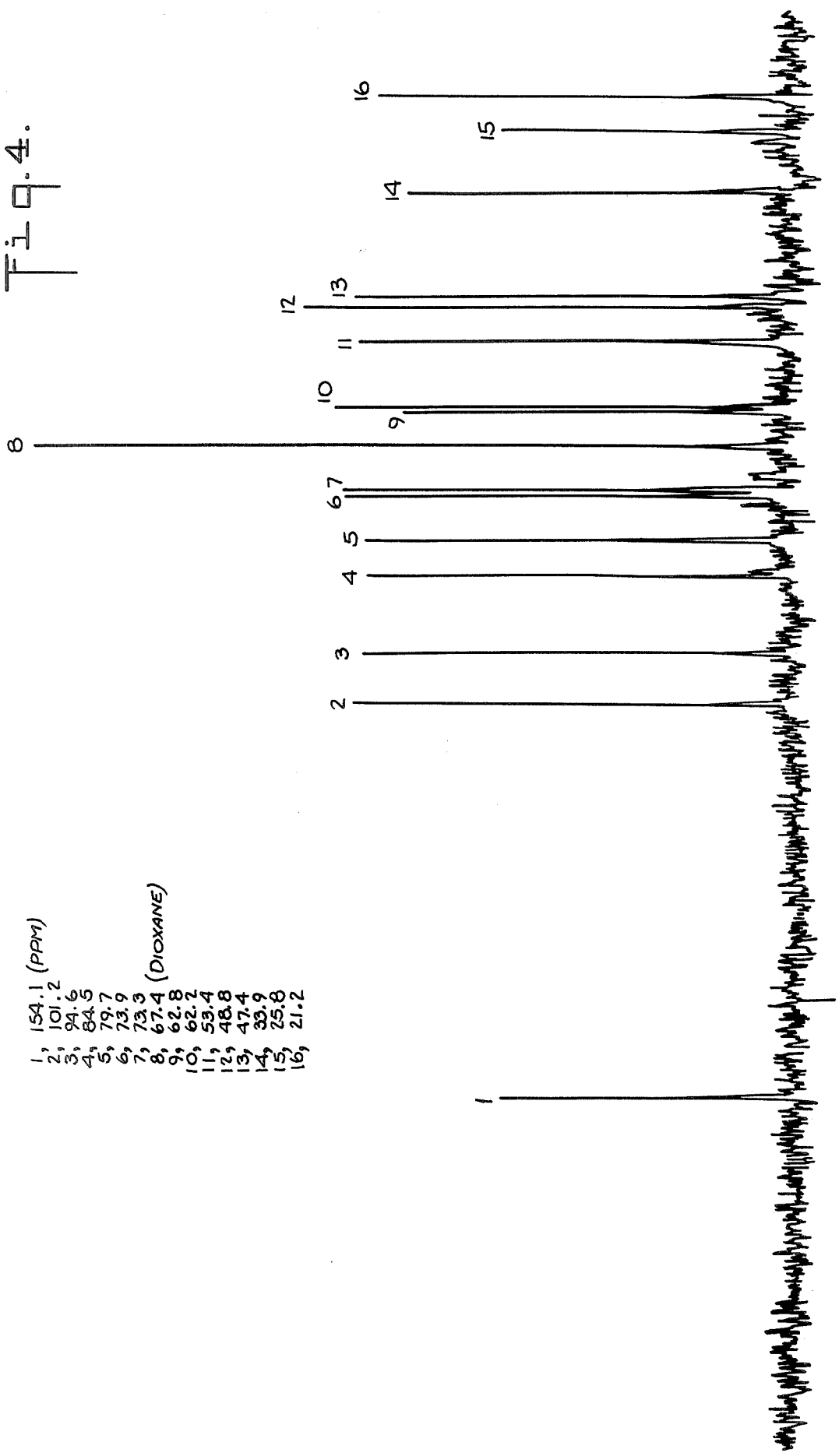

(8) The CMR spectrum of Fortimicin KG, measured in a deuterium oxide solution (pD=10.6) using a JEOL PFT-100A spectrometer is illustrated in FIG. 4.
(9) The mass spectrum of the substance reveals the following M ion and fragment ions. The formula in parentheses means the composition formula obtained by high resolution mass spectrometry.

| m/e | 346 ($C_{15}H_{30}N_4O_5$), | |
| --- | --- | --- |
| | 247 ($C_{10}H_{21}N_3O_4$), | 235 ($C_9H_{19}N_2O_5$), |
| | 217 ($C_9H_{17}N_2O_4$), | 189 ($C_8H_{17}N_2O_3$) |

From the result of the mass spectrometry, the molecular weight of the substance is calculated to be 346 and the molecular formula is calculated to be $C_{15}H_{30}N_4O_5$. The elementary analytical values of the substance (hydrated with 2 moles of $H_2O$) as calculated from the molecular formula are C=47.11%, H=8.96% and N=14.65%.
(10) Based on the foregoing physicochemical data, the structural formula of Fortimicin KG is considered to be as follows:

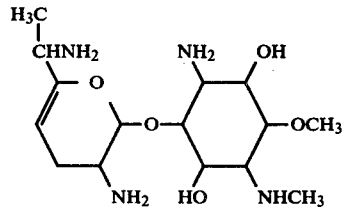

(11) The free base of Fortimicin KG is very soluble in water, soluble in methanol and slightly soluble in ethanol and acetone but is insoluble in organic solvents such as chloroform, benzene, ethyl acetate, butyl acetate, ether, butanol, petroleum ether, n-hexane, and the like.
(12) The Rf values of Fortimicin KF and Fortimicin KG in paper chromatography and thin layer chromatography using various developers are shown in the following Tables 1 to 3. For comparison, the Rf values of antibiotics which are considered to be similar to Fortimicin KF and Fortimicin KG are also described.

Table 1

Rf values of Fortimicin KF and Fortimicin KG in ascending paper chromatography (at 28° C.)

| Developer | Rf value KF | Rf value KG | Period of development (hour) |
|---|---|---|---|
| 20% ammonium chloride | 0.96 | 0.96 | 3 |
| water-saturated n-butanol | 0.00 | 0.00 | 15 |
| n-butanol:acetic acid:water (3:1:1) (by volume) | 0.06 | 0.06 | 15 |
| water-saturated ethyl acetate | 0.00 | 0.00 | 4 |
| water-saturated n-butanol containing 2% (W/V) p-toluene sulfonic acid and 2% (W/V) piperidine | 0.04 | 0.04 | 15 |

Table 2

Rf values in silica gel thin layer chromatography (at room temperature; ater three hours of development)

| Developer* | Antibiotic | Rf value |
|---|---|---|
| I | Fortimicin KF | 0.72 |
| " | Fortimicin KG | 0.77 |
| " | Fortimicin B | 0.80 |
| " | Fortimicin A | 0.74 |
| " | Fortimicin C | 0.75 |
| " | Fortimicin D | 0.69 |
| II | Fortimicin KF | 0.35 |
| " | Fortimicin KG | 0.39 |
| " | Fortimicin B | 0.62 |
| " | Fortimicin A | 0.37 |
| " | Fortimicin C | 0.40 |
| " | Fortimicin D | 0.37 |

*Developer I: The upper layer of chloroform, methanol and 17% (W/W) aqueous ammonia (2:1:1 by volume).
Developer II: 10% (W/V) ammonium acetate and methanol (1:1 by volume).

Table 3

Rf values of various antibiotics in ascending paper chromatography using the lower layer of chloroform, methanol and 17% aqueous ammonia (2:1:1) as the developer (at room temperature; after 12 hours of development).

| Antibiotics | Rf value |
|---|---|
| Streptomycin A | 0.02 |
| Streptomycin B | 0.00 |
| Bluensomycin | 0.01 |
| Ribostamycin | 0.00 |
| Lividomycin A | 0.00 |
| Lividomycin B | 0.03 |
| Hygromycin B | 0.02 |
| Lividomycin D | 0.02 |
| Spectinomycin | 0.45 |
| Kasugamycin | 0.01 |
| Butirosine A | 0.00 |
| Butirosine B | 0.01 |
| Gentamicin A | 0.00 |
| Gentamicin B | 0.00 |
| Gentamicin $C_{1a}$ | 0.18 |
| Gentamicin $C_1$ | 0.59 |
| Gentamicin $C_2$ | 0.38 |
| Sisomicin | 0.18 |
| Neomycin A | 0.00 |
| Neomycin B | 0.03 |
| Antibiotic No. 460 | 0.01 |
| Neomycin C | 0.00 |
| Kanamycin A | 0.02 |
| Kanamycin B | 0.01 |
| Kanamycin C | 0.02 |
| Paromomycin | 0.00 |

Table 3-continued

Rf values of various antibiotics in ascending paper chromatography using the lower layer of chloroform, methanol and 17% aqueous ammonia (2:1:1) as the developer (at room temperature; after 12 hours of development).

| Antibiotics | Rf value |
|---|---|
| Nebramycin complex | 0.01 |
| Tobramycin | 0.02 |
| Apramycin | 0.02 |
| Nebramycin factor 4 | 0.01 |
| Nebramycin factor 5 | 0.00 |
| Myomycin | 0.00 |
| XK-62-2 (Sagamicin) | 0.49 |
| Fortimicin B | 0.65 |
| Fortimicin A | 0.37 |
| Fortimicin C | 0.18 |
| Fortimicin D | 0.18 |
| Fortimicin KF | 0.40 |
| Fortimicin KG | 0.55 |
| Fortimicin KE | 0.59 |

In the following Table 4, the antibacterial spectra of Fortimicin KF and Fortimicin KG against various microorganisms are set forth.

Table 4

(Minimum Inhibitory Concentration, γ/ml measured by agar dilution method at pH 8.0)

| Microorganism | MIC (γ/ml) KF | MIC (γ/ml) KG |
|---|---|---|
| *Bacillus subtilis* No. 10707 | 4.2 | 4.5 |
| *Staphylococcus aureus* ATCC 6538P | 2.1 | 1.1 |
| *Klebsiella pneumoniae* ATCC 10031 | 4.2 | 4.5 |
| *Escherichia coli* ATCC 26 | 4.2 | 4.5 |
| *Shigella sonnei* ATCC 9290 | 8.4 | 9.0 |
| *Salmonella typhosa* ATCC 9992 | 4.2 | 2.3 |
| *Proteus vulgaris* ATCC 6897 | 4.2 | 4.5 |

As is apparent from the above, Fortimicin KF and Fortimicin KG exhibit strong antibacterial activity against a broad range of Gram-positive and Gram-negative bacteria. In view thereof, Fortimicin KF and Fortimicin KG are applicable to medicinal purposes and to sterilization of instruments as antibacterial agents. Fortimicin KF and Fortimicin KG are also useful as starting materials for chemical modification to synthesize various derivative thereof.

A comparison of Fortimicin factors KF and KG with known antibiotics further illustrates their novelty. As water-soluble, basic antibiotics produced by microorganisms of the genus Micromonospora and having a broad antibacterial spectra, these are the gentamicin complex (M. J. Weinstein et al.: Antimicrobial Agents and Chemotherapy, 1963, 1; D. J. Cooper et al.: J. Infect. Dis. 119, 342, 1969; and J. A. Waitz et al.: Antimicrobial Agents and Chemotherapy 2, 464, 1972), antibiotic No. 460 (Japanese Patent Publication No. 16153/71), sisomicin (M. J. Weinstein et al.: J. Antibiotics, 23, 551, 555, 559, 1070), XK-62-2 (U.S. Pat. No. 4,045,298), Fortimicin B, Fortimicin A, Fortimicin C, Fortimicin D and Fortimicin KE, all of which are described in the U.S. patent and application referred above.

As shown in the above Table 3, gentamicin A and B components show Rf values of 0.00 and 0.00 respectively in the paper chromatography. On the other hand, in the same paper chromatography, Rf values of Fortimicin KF and fortimicin KG are 0.40 and 0.55, respectively. Thus, Fortimicin KF and Fortimicin KG are clearly different from the gentamicin components. Comparing Fortimicin KF and Fortimicin KG with antibiotic No. 460, sisomicin, XK-62-2, Fortimicin B, Fortimicin A, Fortimicin C, Fortimicin D and Fortimicin KE, as is apparent from Table 3, antibiotic No. 460, sisomicin, XK-62-2, Fortimicin B, Fortimicin A, Fortimicin C, Fortimicin D and fortimicin KE show Rf values of 0.01, 0.18, 0.49, 0.65, 0.37, 0.18, 0.18 and 0.59 respectively, whereas the Rf values of Fortimicin KF and Fortimicin KG are 0.40 and 0.55 in the same paper chromatography and, therefore, are different from these antibiotics.

In addition, as water-soluble, basic antibiotics produced by actinomycetes other than those of the genus Micromonospora and having a broad range of antibacterial spectra, streptomycin, ribostamycin, lividomycin A, spectinomycin, kasugamycin, neomycin, kanamycin, nebramycin, and paromomycin may be mentioned. Fortimicin KF and Fortimicin KG have been found to be greatly different from any of these antibiotics in the physicochemical properties. Moreover, as is apparent from Table 3, Fortimicin KF and Fortimicin KG are quite different from these antibiotics in Rf values in paper chromatography.

From the foregoing, Fortimicin KF and Fortimicin KG are considered to be new antibiotic compositions of matter.

Fortimicin factors KF and KG are produced by fermentation of a microorganism belonging to the genus Micromonospora. Any strain belonging to the genus Micromonospora and capable of forming Fortimicin KF and/or Fortimicin KG in the culture liquor may be used. Examples of strains are *Micromonospora olivoasterospora* MK-70 (FERM-P No. 1560) (ATCC 21819), *Micromonospora olivoasterospora* MK-80 (FERM-P No. 2192) (ATCC 31010) and *Micromonospora olivoasterospora* Mm 744 (FERM-P No. 2193) (ATCC 31009). These strains have been deposited with the American Type Culture Collection, Rockville, Md. U.S.A. and with the Fermentation Research Institute, Agency of Industrial Science and Technology, Chiba City, Japan and have been accorded the accession numbers noted above. The microbiological properties of these strains are described in U.S. Pat. No. 3,931,400, which description is expressly incorporated herein by reference.

As is the case with other strains of Actinomycetes, the microorganisms useful in carrying out the present invention can be mutated by artificial means such as ultraviolet irradiation, X-ray irradiation and use of various mutation including chemicals in known manner to enhance the production of metabolic products, an example of which is *Micromonospora olivoasterospora* CS-26 (FERM-P No. 3567, NRRL 8178). This latter mutant has been deposited with the U.S. Department of Agriculture, Peoria, Ill., and is freely available to the public.

Generally, conventional methods for culturing Actinomycetes may be employed in the process of the present invention. Thus, various nutrient sources may be used for the culture medium. Appropriate carbon sources include glucose, starch, mannose, fructose, sucrose, molasses, etc. either alone or in combination. Hydrocarbons, alcohols, organic acids, etc. may also be used depending upon the assimilability possessed by the microorganisms utilized. As inorganic and organic nitrogen sources, ammonium chloride, ammonium sulfate, urea, ammonium nitrate, sodium nitrate, etc. may be used either alone or in combination or natural nitrogen sources, such as peptone, meat extract, yeast extract, dry yeast, corn steep liquor, soybean powder, casamino acid, soluble vegetable protein, etc. may be utilized. If necessary, inorganic salts such as sodium chloride, potassium chloride, calcium carbonate, phosphates, etc. may be added to the medium as well as any other organic and inorganic materials which promote the growth of the organism and the production of Fortimicin KF and/or Fortimicin KG.

A liquid culturing method, particularly, a submerged stirring culturing method is most suitable. Culturing temperature is desirably 25°–40° C. and it is preferred to carry out culturing at around neutral pH. Usually, after 2 to 15 days of culturing, Fortimicin KF and/or Fortimicin KG are formed and accumulated in the culture liquor. When the yield of the antibiotic in the culture liquor reaches a maximum, culturing is discontinued and the desired product is isolated and purified from the culture liquor.

Isolation and purification of Fortimicin KF and Fortimicin KG is carried out by methods usually used for the isolation and purification of microbial metabolic products from a culture liquor.

Since the antibiotics Fortimicin KF and Fortimicin KG are basic substances and are readily soluble in water but poorly soluble in the ordinary organic solvents, the antibiotics can be purified by the methods usually used for the purification of so-called water-soluble basic antibiotics. More specifically, Fortimicin KF and Fortimicin KG can be purified by a proper combination of adsorption and desorption from cation exchange resin, cellulose column chromatography, adsorption and desorption using a column of Sephadex LH-20, silica gel column chromatography, etc. As an example, a suitable method of purification of Fortimicin KF and Fortimicin KG from the culture liquor when a strain capable of producing Fortimicin complex (a mixture containing Fortimicin factors A, B, C, D, KE, KF, and KG and by-products having antibacterial activity) is used is as follows. The cell-free culture filtrate is adjusted to pH 7.5 and is then passed through a cation exchange resin such as Amberlite IRC-50 (ammonium form) (Rohm & Haas Co., U.S.A.). After the resin is washed with water, elution is carried out with 0.5 N aqueous ammonia. The active fractions are combined and concentrated under reduced pressure. The concentrate is treated with an anion exchange resin, Dowex 1×2 (OH form) (The Dow Chemical Co., U.S.A). The active fractions obtained by the elution are combined and concentrated under reduced pressure to obtain a crude powder of Fortimicin complex. The crude powder is dissolved in water, and then the solution is adjusted to a pH of 5.0 with 2 N sulfuric acid and then passed through a column packed with active carbon. The active principles are adsorbed on the active carbon. The active carbon is then washed with water to remove impurities, which are not adsorbed on the active carbon, as effluent. Thereafter, elution is carried out with 0.2 N sulfuric acid to elute the active principles. The active fractions are combined and, after neutralization with an anion exchange resin, Dowex 44 (OH form) (The Dow Chemical Co., U.S.A.), freeze-dried to obtain the free base of each component of the Fortimicin complex. The freeze-dried powder is dissolved in water and the pH of the solution is adjusted to 7.5 with 2 N-sulfuric acid. The solution is passed through a column packed with a cation exchange resin Amberlite CG-50 type 1 (ammonium form) (Rohm and Haas Co., U.S.A.). After the column is washed with water, elution is carried out with 0.2 N aqueous ammonia. After several trace components are eluted out, a mixture of Fortimicin B, Fortimicin KE and Fortimicin KG is eluted in a large active fraction. Then, several trace components are eluted, followed by a mixture of Fortimicin A, Fortimicin KF and Fortimicin D. Each of the mixtures are concentrated to dryness to obtain the free base thereof in powdered form.

The crude powders are then subjected to silica gel column chromatography using a mixed solvent of chloroform, ethanol, aqueous ammonia and acetone (2:2:1:2, by volume) as a developer. The crude powder containing Fortimicin factors B, KE and KG is suspended in the solvent and introduced into the column. Development is carried out with the same solvent at a flow rate of about 30 ml/hour. First, Fortimicin B and Fortimicin KE are eluted and then Fortimicin KG is eluted. The active fractions containing Fortimicin KG are collected and concentrated under reduced pressure. The concentrate is freeze-dried to obtain the free base of Fortimicin KG.

When the mixture of Fortimicin factors A, KF and D is subjected to silica gel column chromatography in the same manner as described above, first, Fortimicin KF is eluted. Then, Fortimicin A and Fortimicin D are eluted. The fractions containing Fortimicin KF are collected and concentrated under reduced pressure to obtain a residue. After the residue is dissolved in water, the solution is freeze-dried to obtain the free base of Fortimicin KF.

By the foregoing procedure, Fortimicin KF and Fortimicin KG can be obtained in considerably purified form. However, sometimes impurities are present in the samples. In such case, the samples are also subjected to cellulse column chromatography. As the developer, a mixed solvent of n-butanol, pyridine, acetic acid and water (3:2:1:2 by volume) is used. The active fractions obtained by elution are combined and concentrated under reduced pressure to obtain a purified preparate of Fortimicin KF or Fortimicin KG. For the removal of impurities which exhibit a positive reaction with ninhydrin, column chromatography using carboxymethylcellulose is also effective. More specifically, in this case, a solution of the crude powder is passed through a column packed with carboxymethylcellulose (ammonium form). The active principles are adsorbed on carboxymethylcellulose. Then, the column is thoroughly washed with water to elute most of the pigments and inorganic salts. Thereafter, elution is carried out with 0.2 N ammonium bicarbonate to elute the active principles. Fractions containing Fortimicin KF or Fortimicin KG are combined and freeze-dried to obtain purified Fortimicin KF or Fortimicin KG.

During the above-described purification procedures, the fractions are checked by silica gel thin layer chromatography. As the developer, a mixed solvent of chloroform, ethanol, concentrated aqueous ammonia and acetone (2:2:1:2 by volume) is used and development is carried out at room temperature for 2 hours. Fortimicin KF and Fortimicin KG show Rf values of about 0.50 and 0.56 respectively.

Preparation of non-toxic acid addition salts of Fortimicin KF and fortimicin KG, including the mono-, di-, tri- and tetra-salts, is carried out using known procedures such as by reacting one molecule of Fortimicin KF or Fortimicin KG with 1-4 equivalent of a pharmaceutically acceptable non-toxic acid. Appropriate non-toxic acid include the inorganic acids such as hydrochloric acid, hydrobromic acid, hydroiodic acid, sulfuric acid, phosphoric acid, carbonic acid, nitric acid, etc. and organic acids such as acetic acid, fumaric acid, malic acid, citric acid, mandelic acid, ascorbic acid, tartaric acid, succinic acid, maleic acid, the like.

Certain specific embodiments of the invention are illustrated by the following representative examples.

EXAMPLE 1

A. Culturing of the CS-26 strain

In this Example, *Micromonospora olivoasterospora* CS-26 (NRRL 8178) (FERM-P No. 3567) is used as the need strain. The seed strain is a mutant strain derived from *Micromonospora olivoasterospora* MK-70 (ATCC 21819) (FERM-P No. 1560) by means of treatment with nitrosoquanidine, ultraviolet irradiation and γ-ray irradiation. A medium comprising 2 g/dl glucose, 0.5 g/dl peptone, 0.5 g/dl yeast extract and 0.1 g/dl calcium carbonate (pH 7.5 before sterilization) is used as a first seed medium. A loopful of the seed strain is inoculated into 10 ml portions of the first seed medium in 50 ml-large test tubes and is cultured at 30° C. for 5 days. 10 ml of the thus prepared first seed culture is inoculated into 30 ml portions of a second seed medium in 250 ml-Erlenmeyer flasks. The second seed medium has the same composition as that of the first seed medium. The second seed culturing is carried out with shaking at 30° C. for 2 days. Then, 30 ml of the second seed culture is inoculated into 300 ml portions of a third seed medium in 2 L.-Erlenmeyer flasks provided with baffles. The third seed medium has the same composition as that of the first seed medium. The third seed culturing is carried out with shaking at 30° C. for 2 days. Then 1.5 L. of the third seed culture (corresponding to 5 flasks) is inoculated into 15 L. of a fourth seed medium in a 30 L.-stainless steel jar fermenter. The fourth seed medium has the same composition as that of the first seed medium. The fourth seed culturing in the jar fermenter is carried out with aeration and stirring (revolution: 350 r.p.m.; aeration: 15 L./min) at 37° C. for 2 days. Then 15 L. of the fourth seed culture is inoculated into 150 L. of a fermentation medium in a 300 L.-fermenter. The fermentation medium has the following composition.

| | |
|---|---|
| Soluble starch | 4 g/dl |
| Soybean meal | 2 g/dl |
| Corn steep liquor | 1 g/dl |
| $K_2HPO_4$ | 0.05 g/dl |
| $MgSO_4 \cdot 7H_2O$ | 0.05 g/dl |
| KCl | 0.03 g/dl |
| $CaCO_3$ | 0.1 g/dl |
| (pH 7.5 before sterilization) | |

Fermentation in the fermenter is carried out with aeration and stirring (revolution: 150 r.p.m.; aeration: 80 L./min) at 37° C. for 4 days.

B. Isolation of crude Fortimicin complex

After the completion of fermentation, the culture liquor is adjusted to pH 2.5 with concentrated sulfuric acid and is stirred for 30 minutes. Thereafter, about 7 kg of a filter aid, Radiolite No. 600 (product of Showa Kagaku Kogyo Co., Ltd.) is added to the culture liquor and the microbial cells are removed by filtration. The filtrate is adjusted to pH 7.5 by the addition of 6 N sodium hydroxide. The resulting filtrate is passed through a column packed with about 20 L. of a cation exchange resin, Amberlite IRC-50 (ammonia form).

The active principles are adsorbed on the resin. After the resin is washed with water, elution of the active principles is carried out with 1 N aqueous ammonia. The eluate is subjected to determination of activity by a paper disc method using an agar plate of *Bacillus subtilis* No. 10707. Fractions showing activity are combined and concentrated under reduced pressure to about 1 L. The concentrate is passed through a column packed with 500 ml of an anion exchange resin, Dowex 1×2 (OH form) and then about 2 L. of water is passed through the column. In this manner, impurities are removed and the active principles are eluted with water. The active fractions are combined and concentrated under reduced pressure to about 100 ml. The concentrate is then passed through a column packed with about 50 ml of active carbon powder. The active principles are adsorbed on the active carbon. The column is washed with water. The effluent and washings are discarded. Elution is then carried out with 0.2 N sulfuric acid. The eluate is subjected to determination of activity by a paper disc method using *Bacillus subtilis* No. 10707. The active fractions are combined and passed through a column of an anion exchange resin, Dowex 44 (OH form) and elution of the active principles is carried out with water. The active fractions are combined and concentrated to about 60 ml. The concentrate is then freeze-dried to obtain a crude powder of Fortimicin complex. The yield of the crude powder is about 40 g.

C. Isolation and purification of Fortimicin KF

To isolate and purify Fortimicin KF, 20 g of the crude powder obtained in the preceding process B is dissolved in 30 ml of water and the pH of the solution is adjusted to 7.5 with concentrated sulfuric acid. Then the solution is passed through a column packed with 1 L. of a cation exchange resin, Amberlite CG-50 (ammonium form) to adsorb the active principles thereon. After the resin is washed with water, elution is carried out with 0.2 N-aqueous ammonia. The eluate is recovered in 50 ml fractions and the activity of each of the fractions is determined by a paper disc method and thin layer chromatography. First, several trace components are eluted, and next a large active component and several trace components are eluted. Then, a mixture of Fortimicin factors A, KF and D is eluted. This mixture is concentrated to dryness to obtain a powder comprising the free base thereof.

The powder is charged over about 500 ml of silica gel in a glass column to form a uniform, thin layer. The silica gel is previously suspended in a mixed solvent of chloroform, ethanol, concentrated aqueous ammonia and acetone (2:2:1:2 by volume), and packed in the glass column to form a tight, uniform layer. The column is then thoroughly washed with the same solvent. After the crude powder is charged, the solvent having the same composition as described above is poured gradually into the column from the top and thereafter elution is carried out continuously at a flow rate of 50 ml/hour. The eluate is recovered in 20 ml fractions and the activity of each of the fractions is determined by a paper disc method using *Bacillus subtilis* No. 10707. First, Fortimicin KF is eluted followed by Fortimicin A and Fortimicin D. The active fractions are subjected to thin layer chromatography. The fractions containing Fortimicin KF are collected and concentrated under reduced pressure to remove the solvent.

The residue is dissolved in a small amount of water and then the solution is freeze-dried to obtain about 2 g of a purified preparate of the free base of Fortimicin KF. The product exhibits an activity of about 970 units/mg (activity of 1 mg of a pure preparate is defined as 1000 units).

EXAMPLE 2

In this example, the same strain, seed medium (the first through fourth seed media) and fermentation medium as in Example 1 are used and the same culturing and purification procedures as in Example 1 are repeated to obtain 40 g of a crude powder of Fortimicin complex.

Then, 20 g of the crude powder thus obtained is dissolved in 30 ml of water and pH of the solution is adjusted to 7.5 with concentrated sulfuric acid. Then the solution is passed through a column packed with 1 L. of a cation exchange resin, Amberlite CG-50 (ammonium form) to adsorb the active principles thereon. After the resin is washed with water, elution is carried out with 0.2 N-aqueous ammonia. The eluate is recovered in 50 ml fractions and the activity of each of the fractions is determined by a paper disc method and thin layer chromatography. First, several trace components are eluted, and next a large active component, a mixture of Fortimicin factors B, KE and KG is eluted. The mixture is concentrated to dryness to obtain a powder comprising the free base thereof.

This powder is charged over about 500 ml of silica gel in a glass column to form a uniform, thin layer. The silica gel is previously suspended in a mixed solvent of chloroform, ethanol, concentrated aqueous ammonia and acetone (2:2:1:2 by volume), and packed in the glass column to form a tight, uniform layer. The column is then thoroughly washed with the same solvent. After the powder is charged, the solvent having the same composition as described above is poured gradually into the column from the top and thereafter elution is carried out continuously at a flow rate of 50 ml/hour. The eluate is recovered in 20 ml fractions and the activity of each of the fractions is determined by a paper disc method using *Bacillus subtilis* No. 10707. First, Fortimicin B and Fortimicin KE are eluted and next Fortimicin KG is eluted. The active fractions are subjected to thin layer chromatography. The fractions containing Fortimicin KG are collected and concentrated under reduced pressure to remove the solvent.

The residue is then dissolved in a small amount of water, and the solution is freeze-dried to obtain about 5 g of a purified preparate of the free base of Fortimicin KG. The product exhibits an activity of about 970 units/mg (activity of 1 mg of a pure preparate is defined as 1000 units).

EXAMPLE 3

In this example, the same strain and seed medium (the first through fourth seed media) as in Example 1 are used except that a fermentation medium consisting of 4 g/dl soluble starch, 3 g/dl Ebios (dry yeast powder), 0.05 g/dl $K_2HPO_4$, 0.05 g/dl $MgSO_4 7H_2O$, 0.03 g/dl KCl and 0.1 g/dl $CaCO_3$ is used and the same culturing and purification procedures as in Example 1 are repeated to obtain 68 g of a crude powder of Fortimicin complex.

Then 40 g of the crude powder is purified in the same manner as in Examples 1 and 2 to obtain 13 g of Fortimicin KG and 6 g of Fortimicin KF, each exhibiting an activity of 860 units/mg. For further purification, these preparates are subjected to cellulose column chromatography. About 300 ml of a cellulose powder (AVICEL, a product of Funakoshi Seiyaku K.K.) is packed in a glass column. The preparate is charged over the cellulose powder to form a uniform, thin layer. The cellulose powder is previously suspended in a mixed solvent of n-butanol, acetic acid, pyridine and water (6:2:4:4 by volume) and packed in the glass column to form a tight, uniform layer. The column is then thoroughly washed with the same solvent. After the preparate is charged, the same solvent is poured gradually into the column from the top and thereafter elution is carried out continuously at a flow rate of about 1 ml/min. The eluate is recovered in 7 ml fractions and the activity of each of the fractions is determined by a paper disc method using *Bacillus subtilis* No. 10707. The active fractions are combined and concentrated under reduced pressure to substantially remove the solvent. The residue is dissolved in a small amount of water and freeze-dried. In this manner, about 10 g of a purified preparate of the free base of Fortimicin KG exhibiting an activity of 980 units/mg is obtained.

In the same manner as above, purification is carried out to obtain about 4 g of a purified preparate of the free base of Fortimicin KF exhibiting an activity of 980 units/mg.

EXAMPLE 4

In this example, the same strain and seed medium (the first through fourth media) as in Example 1 are used except using a fermentation medium comprising 4 g/dl starch, 3 g/dl casamino acid (acid hydrolyzate of casein, DIFCO, Co., U.S.A.) 0.05 g/dl $K_2HPO_4$, 0.05 g/dl $MgSO_4.7H_2O$, 0.03 g/dl KCl and 0.1 g/dl $CaCO_3$ and the same culturing, purifying and isolating procedures as in Example 1 are repeated to obtain 10 g of Fortimicin KG exhibiting an activity of 985 units/mg and 4 g of Fortimicin KF exhibiting an activity of 985 units/mg.

What is claimed is:

1. Fortimicin KF, a composition of matter having antibacterial activity and having the structural formula

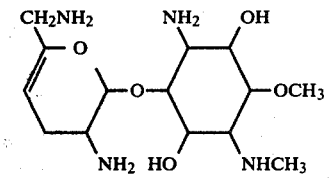

and the pharmaceutically acceptable non-toxic acid addition salts thereof.

2. Fortimicin KG, a composition of matter having antibacterial activity and having the structural formula

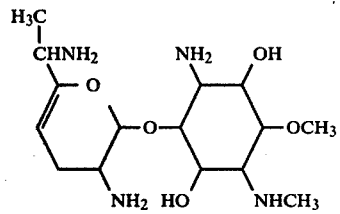

and the pharmaceutically acceptable non-toxic acid addition salts thereof.

* * * * *